US008700333B2

(12) United States Patent
Roberts (10) Patent No.: US 8,700,333 B2
(45) Date of Patent: Apr. 15, 2014

(54) APPARATUS AND ALGORITHM FOR MEASURING FORMATION BULK DENSITY

(75) Inventor: Loren P. Roberts, Humble, TX (US)

(73) Assignee: Baker Hughes Incorporated, Houston, TX (US)

( * ) Notice: Subject to any disclaimer, the term of this patent is extended or adjusted under 35 U.S.C. 154(b) by 371 days.

(21) Appl. No.: 13/016,381

(22) Filed: Jan. 28, 2011

(65) Prior Publication Data

US 2011/0191030 A1    Aug. 4, 2011

Related U.S. Application Data

(60) Provisional application No. 61/300,233, filed on Feb. 1, 2010.

(51) Int. Cl.
  *G01V 1/40*   (2006.01)
  *G01V 3/18*   (2006.01)
  *G01V 5/04*   (2006.01)

(52) U.S. Cl.
  USPC .................................................. 702/8; 702/11

(58) Field of Classification Search
  USPC ................................................. 702/8, 11, 137
  See application file for complete search history.

(56) References Cited

U.S. PATENT DOCUMENTS

| | | | |
|---|---|---|---|
| 4,297,575 A | 10/1981 | Smith, Jr. et al. | |
| 4,415,804 A | 11/1983 | Sowerby | |
| 5,608,215 A * | 3/1997 | Evans | 250/269.6 |
| 5,900,627 A | 5/1999 | Odom et al. | |
| 6,376,838 B1 | 4/2002 | Odom | |
| 6,936,812 B2 | 8/2005 | Odom et al. | |
| 7,117,092 B2 * | 10/2006 | Jacobson | 702/8 |
| 7,294,829 B2 | 11/2007 | Gilchrist | |
| 7,491,929 B2 | 2/2009 | Truax | |
| 7,573,027 B2 | 8/2009 | Huiszoon | |
| 7,791,017 B2 | 9/2010 | Stephenson et al. | |
| 7,897,914 B2 | 3/2011 | Hall et al. | |
| 7,902,496 B2 | 3/2011 | Botto et al. | |
| 2005/0067160 A1 * | 3/2005 | Jacobson | 166/250.01 |
| 2006/0243898 A1 * | 11/2006 | Gilchrist | 250/269.7 |
| 2007/0252080 A1 * | 11/2007 | Truax | 250/269.6 |
| 2009/0039242 A1 | 2/2009 | Botto et al. | |
| 2010/0145621 A1 | 6/2010 | Moake | |
| 2010/0187412 A1 | 7/2010 | Grant et al. | |
| 2010/0193676 A1 | 8/2010 | Jacobson et al. | |
| 2010/0252724 A1 | 10/2010 | Inanc et al. | |
| 2010/0314535 A1 * | 12/2010 | Zhang et al. | 250/252.1 |
| 2010/0332138 A1 | 12/2010 | Inanc et al. | |
| 2011/0035151 A1 | 2/2011 | Botto | |
| 2011/0049345 A1 | 3/2011 | Roberts | |
| 2011/0180697 A1 * | 7/2011 | Inanc et al. | 250/265 |
| 2011/0198489 A1 * | 8/2011 | Roberts | 250/269.3 |
| 2011/0213555 A1 * | 9/2011 | Kopal et al. | 702/6 |

* cited by examiner

*Primary Examiner* — Michael Nghiem
(74) *Attorney, Agent, or Firm* — Mossman Kumar & Tyler PC (57) ABSTRACT

The present disclosure relates to borehole logging methods and apparatuses for estimating formation properties using nuclear radiation, particularly an apparatus and method for estimating bulk density of a formation. The method may include using gamma ray count rate information to model bulk density. The method may include using time-dependent ratios with a pulsed radiation source. The method may also include dividing gamma ray information by time and/or by energy window. The apparatus includes a processor and storage subsystem with a program that, when executed, implements the method.

18 Claims, 9 Drawing Sheets

APPARATUS AND ALGORITHM FOR MEASURING FORMATION BULK DENSITY

CROSS-REFERENCES TO RELATED APPLICATIONS

This application claims priority from U.S. Provisional Patent Application Ser. No. 61/300,233 filed on 1 Feb. 2010.

FIELD OF THE DISCLOSURE

In one aspect, this disclosure generally relates to borehole logging methods and apparatuses for estimating formation properties using nuclear radiation based measurements. More particularly, this disclosure relates to estimating one or more formation parameters of interest using information obtained from an earth formation exposed to a pulsed neutron source.

BACKGROUND OF THE DISCLOSURE

Oil well logging has been known for many years and provides an oil and gas well driller with information about the particular earth formation being drilled. In conventional oil well logging, during well drilling and/or after a well has been drilled, a radiation source and associated radiation detectors may be conveyed into the borehole and used to determine one or more parameters of interest of the formation. A rigid or non-rigid carrier is often used to convey the radiation source, often as part of a tool or set of tools, and the carrier may also provide communication channels for sending information up to the surface.

SUMMARY OF THE DISCLOSURE

In aspects, the present disclosure is related to methods of estimating a parameter of interest of a formation using radiation detected from a subterranean formation.

One embodiment according to the present disclosure may be a method for estimating the bulk density of an earth formation, comprising: estimating the bulk density using a model relating inelastic gamma ray information above an energy level required for pair production acquired from a first detector to inelastic gamma ray information acquired from a second detector. The inelastic gamma ray information from the first and second detectors may be time-dependent.

Another embodiment according to the present disclosure may be a method for estimating bulk density of an earth formation, comprising: estimating the bulk density using a model relating inelastic gamma ray information above an energy level required for pair production acquired from a first detector to inelastic gamma ray information acquired from a second detector dividing the inelastic gamma ray information acquired from the first detector into at least two energy windows, wherein a first energy window of the at least two energy windows is above the energy level required for pair production; dividing the inelastic gamma ray information acquired from the second detector into the at least two energy windows; and reducing an error due to pair production using the inelastic gamma ray information acquired from the first detector in the first energy window and the inelastic gamma ray information acquired from the second detector in a second energy window of the at least two energy windows Another embodiment according to the present disclosure may be an apparatus for estimating bulk density of an earth formation, comprising: a processor; a subsystem non-transitory computer-readable medium; and a program stored by the non-transitory computer-readable medium comprising instructions that, when executed, cause the processor to: estimate the bulk density using a model relating inelastic gamma ray information above an energy level required for pair production acquired from a first detector to inelastic gamma ray information acquired from a second detector.

Another embodiment according to the present disclosure may be an apparatus for estimating bulk density of an earth formation, comprising: a processor; a non-transitory computer-readable medium; and a program stored by the non-transitory computer-readable medium comprising instructions that, when executed, cause the processor to: estimate the bulk density using a model relating inelastic gamma ray information above an energy level required for pair production acquired from a first detector to inelastic gamma ray information acquired from a second detector divide the inelastic gamma ray information acquired from the first detector into at least two energy windows, wherein a first energy window of the at least two energy windows is above the energy level required for pair production; divide the inelastic gamma ray information acquired from the second detector into the at least two energy windows; and reduce an error due to pair production using the inelastic gamma ray information acquired from the first detector in the first energy window and the inelastic gamma ray information acquired from the second detector in a second energy window of the at least two energy windows.

Examples of the more important features of the disclosure have been summarized rather broadly in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein.

DETAILED DESCRIPTION

In aspects, this disclosure relates to estimating bulk density of a subterranean formation. Illustrative methods for estimating bulk density may include estimating the reduction in transmission of multiple distinct inelastic gamma rays generated in the formation in the manner of a slab-based or linear transmission bulk density measurement. These estimations may be transmission/attenuation based and supplemented by the Compton scattering information. In many instances, the information used for these estimations may be acquired by tools deployed into a wellbore intersecting one or more formations of interest. Herein, the term "information" may include, but is not limited to, one or more of: (i) raw data, (ii) processed data, and (iii) signals. For context, an exemplary system for deploying and using such tools to acquire this information is described below.

The formation may be exposed to energy, and more particularly a neutron source. Downhole tools may include a radiation source and one or more detectors. Herein, the radiation source may include, but is not limited to, one or more of a neutron source, a gamma-ray source, and an x-ray source. The detectors may be used to detect radiation from the formation, though the detectors are not limited to detecting radiation of the same type as emitted by the radiation source. Detectors may have shielding to prevent the counting of radiation from unintended sources.

Figure 1:
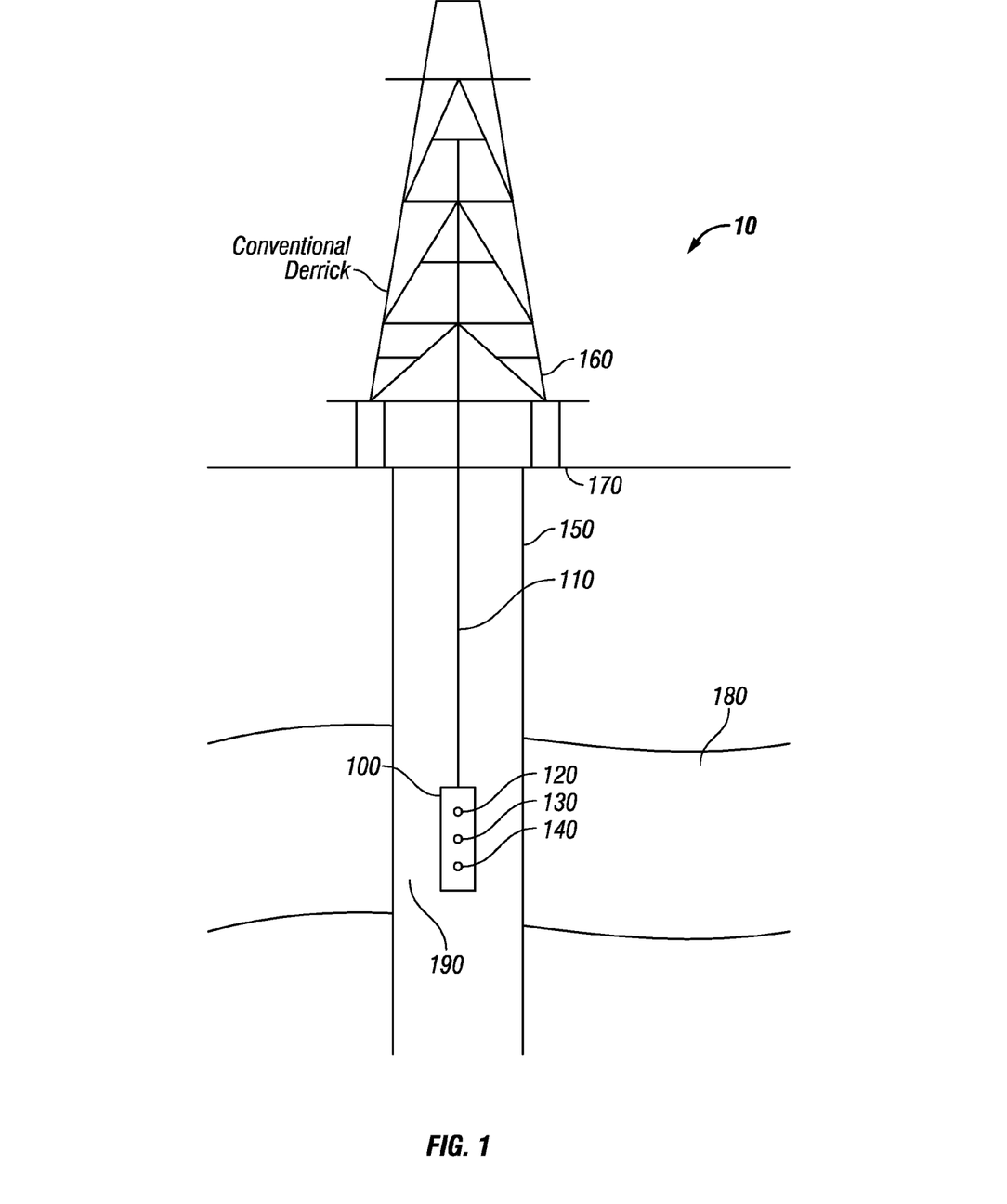
FIG. 1 shows a schematic of a downhole tool deployed in a wellbore along a wireline according to one embodiment of the present disclosure.

FIG. 1 schematically illustrates a drilling system 10 having a downhole tool 100 configured to acquire information for estimating bulk density or another parameter of interest of a formation 180. In one illustrative embodiment, the tool 100 may contain a radiation source 140 and associated detectors 120, 130. The system 10 may include a conventional derrick 160 erected on a derrick floor 170. A carrier 110, which may be rigid or non-rigid, may be configured to convey the downhole tool 100 into wellbore 150 in proximity to formation 180. The carrier 110 may be a drill string, coiled tubing, a slickline, an e-line, a wireline, etc. Downhole tool 100 may be coupled or combined with additional tools (e.g., some or all the information processing system of FIG. 3). Thus, depending on the configuration, the tool 100 may be used during drilling and/or after the wellbore 150 has been formed. The radiation source 140 emits radiation into the formation to be surveyed. This radiation interacts with the nuclei of the atoms of the material of the formation resulting in inelastic gamma rays, capture gamma rays, Compton scattered photons, and pair production photons. In one embodiment, the downhole tool 100 may use a pulsed neutron generator emitting 14.2 MeV fast neutrons as its radiation source 140. The use of 14.2 MeV neutrons from a pulsed neutron source is illustrative and exemplary only, as different energy levels of neutrons may be used. In some embodiments, radiation source 140 may use X-rays. In some embodiments, the radiation source 140 may be continuous. In some embodiments, the radiation source 140 may be controllable in that the radiation source may be turned "on" and "off" while in the wellbore, as opposed to a radiation source that is "on" continuously. This type of radiation source may be called "sourceless" since it does not have a continuous radiation source. Due to the intermittent nature of the pulsed neutron radiation source, the inelastic and capture photons created will reach the detectors 120, 130 during overlapping time periods. Inelastic photons are generated predominantly during the pulse, while capture photons are generated during and after the pulse.

The detectors 120, 130 provide signals that may be used to estimate the radiation counts returning from the formation. Generally, detectors 120, 130 are spaced in a substantially linear fashion relative to the radiation source. If two detectors are used, there may be a short spaced (SS) detector and a long spaced (LS) detector, wherein the detectors have different distances from the radiation source. For instance, in one embodiment, detector 130 may be a short spaced detector, and detector 120 may be a long spaced detector. The SS and LS detectors are not limited to being placed on the same side of the radiation source and their spacing from the radiation source may be the equal or unequal since the response of the detectors does not depend on the spatial variation of the gamma ray source within the formation. Additional detectors may be used to provide additional radiation information. Two or more of the detectors may be gamma ray detectors. Some embodiments may include radiation shielding (not shown), which may be located between radiation source 140 and the detectors 120, 130. Radiation shielding may include, but is not limited to, gamma-ray shielding and neutron shielding. Drilling fluid 190 may be present between the formation 180 and the downhole tool 100, such that emissions from radiation source 140 may pass through drilling fluid 190 to reach formation 180 and radiation induced in the formation 180 may pass through drilling fluid 190 to reach the detectors 120, 130.

In one embodiment, electronics (not shown) associated with the detectors may be configured to record radiation counts from at least two axially spaced detectors 120, 130 with very narrow time bins or windows (on the order of 1 to 1000 microseconds) and generating a time-dependent ratio between the at least two axially spaced detectors by using information from multiple bursts. This ratio may be expressed as a curve or other graphical function that describes a combination of multiple ratio values. In some embodiments, the parameter of interest may be estimated using a difference between the detector counts. Herein, the term time-dependent broadly describes the property of the ratio to vary with time, as opposed to a ratio that remains constant, such as may occur with a continuous radiation source. In some embodiments, the time-dependent ratio may be weighted. The axially spaced detector count rate ratios may be obtained as a function of time and graphically illustrated as a time-dependent ratio curve. Various properties of the formation may be determined using the time-dependent ratio curve, including, but not limited to, bulk density of the formation. In other embodiments, such electronics may be located elsewhere (e.g., at the surface).

Figure 2:
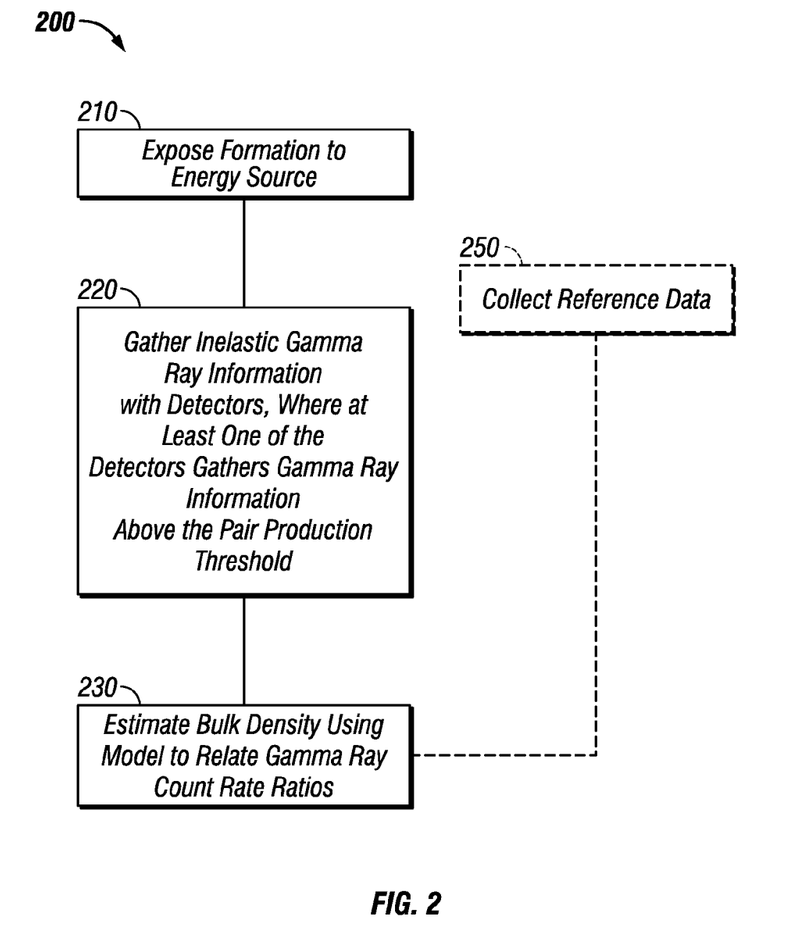
FIG. 2 shows a flow chart of an estimation method for one embodiment according to the present disclosure.

FIG. 2 shows, in flow chart form, one method 200 according to the present disclosure for estimating at least one parameter of interest of the formation 180 (FIG. 1) using a model based on gamma ray information acquired from at least two detectors 120, 130 (FIG. 1). Referring now to FIGS. 1 and 2, method 200 may include step 210, where the radiation source 140 emits radiation in proximity to the formation 180. In step 220, information on inelastic gamma rays may be collected by the detectors 120, 130, where at least one of the detectors 120, 130 is collecting inelastic gamma ray information above the energy threshold required for pair production. In step 230, bulk density of the formation 180 may be estimated by applying one or more inelastic gamma ray count rate ratio(s) to the model. In the alternative, information collected by the detectors 120, 130 may be used to generate a difference between the radiation counts estimated by the detectors 120, 130. The estimation of the bulk density may also include comparison or combination of the gamma ray information with reference information about the formation. In some embodiments, estimation methods 200 may include step 250, where reference information on the formation or formations generally is accessed. Reference information may be combined with gamma ray information in step 230 to estimate bulk density of the formation.

Figure 3:
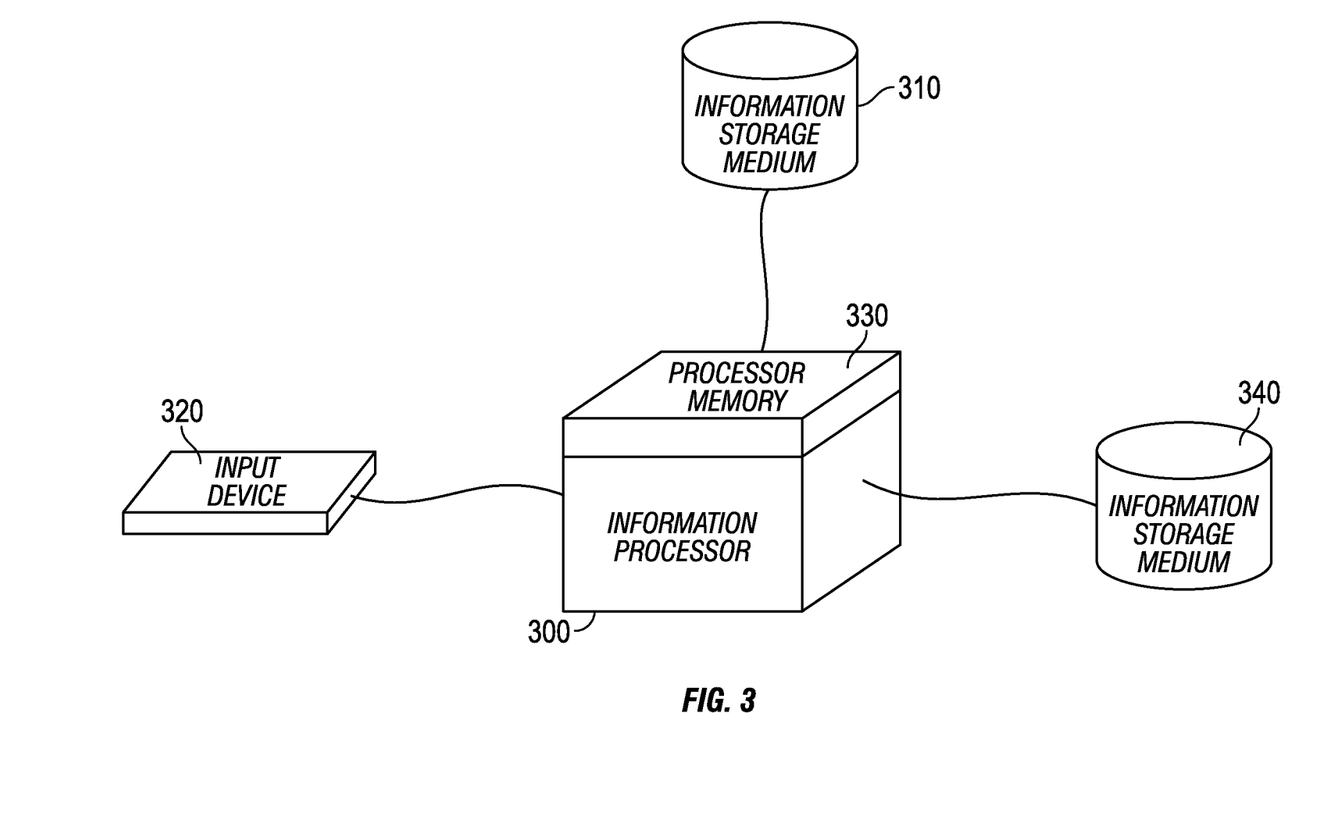
FIG. 3 shows schematic of the apparatus for implementing one embodiment of the method according to the present disclosure.

As shown in FIG. 3, certain embodiments of the present disclosure may be implemented with a hardware environment that includes an information processor 300, an information storage medium 310, an input device 320, processor memory 330, and may include peripheral information storage medium 340. The hardware environment may be in the well, at the rig, or at a remote location. Moreover, the several components of the hardware environment may be distributed among those locations. The input device 320 may be any data reader or user input device, such as data card reader, keyboard, USB port, etc. The information storage medium 310 stores information provided by the detectors. Information storage medium 310 may include any non-transitory computer-readable medium for standard computer information storage, such as a USB drive, memory stick, hard disk, removable RAM, EPROMs, EAROMs, flash memories and optical disks or other commonly used memory storage system known to one of ordinary skill in the art including Internet based storage. Information storage medium 310 stores a program that when executed causes information processor 300 to execute the disclosed method. Information storage medium 310 may also store the formation information provided by the user, or the formation information may be stored in a peripheral information storage medium 340, which may be any standard computer information storage device, such as a USB drive, memory stick, hard disk, removable RAM, or other commonly used memory storage system known to one of ordinary skill in the art including Internet based storage. Information processor 300 may be any form of computer or mathematical processing hardware, including Internet based hardware. When the program is loaded from information storage medium 310 into processor memory 330 (e.g. computer RAM), the program, when executed, causes information processor 300 to retrieve detector information from either information storage medium 310 or peripheral information storage medium 340 and process the information to estimate a parameter of interest. Information processor 300 may be located on the surface or downhole.

Figure 4:
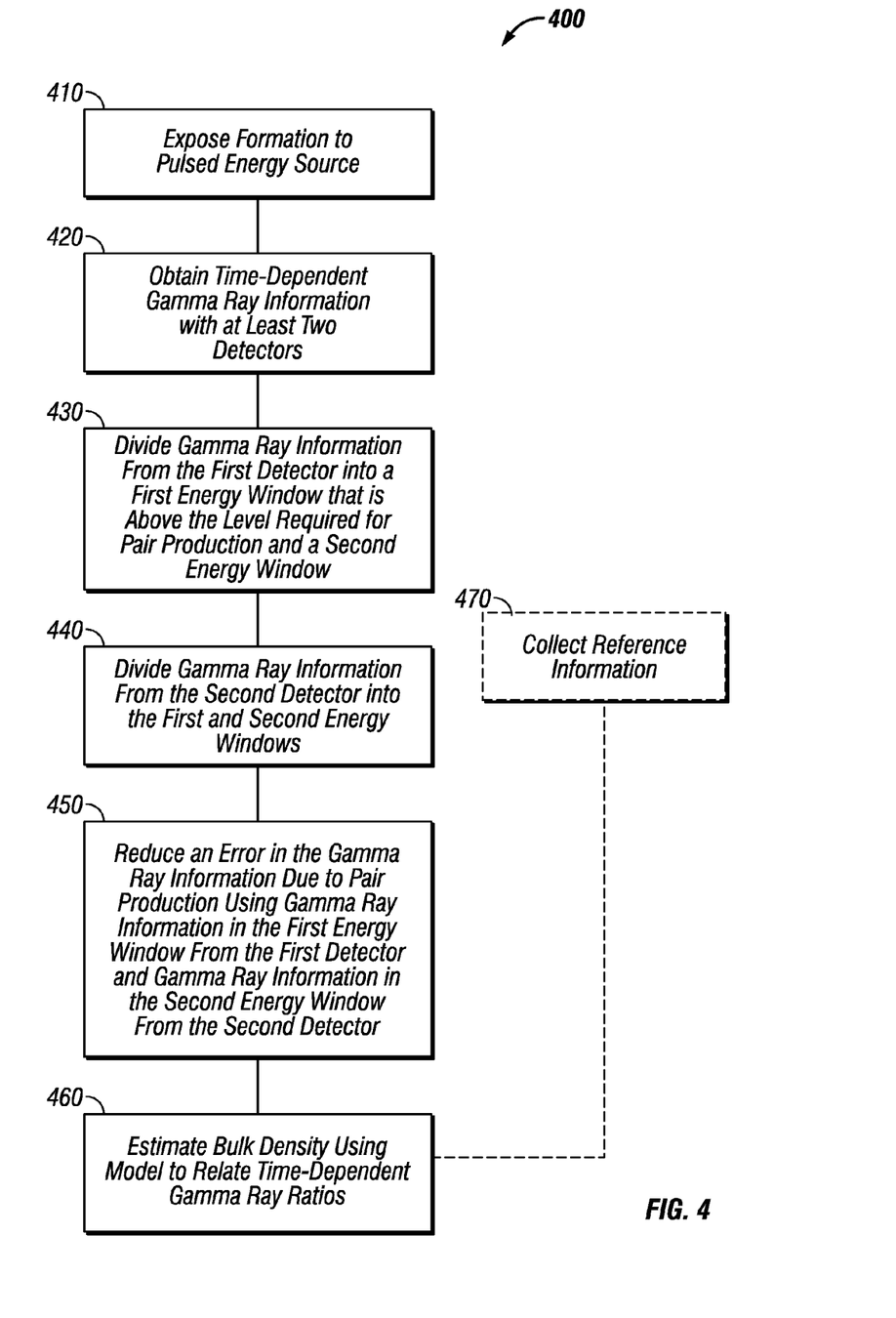
FIG. 4 shows a flow chart of an estimation method for another embodiment according to the present disclosure.

During use, the detectors 120, 130 may gather gamma ray information that is below the energy level required for pair production, since there may be circumstances where lower energy gamma ray information may be useful in determining bulk density. As shown in FIG. 4, one method 400 according to the present disclosure for estimating bulk density of the formation may use a time-dependent ratio based on information acquired from the detectors 120, 130. Method 400 may include step 410, where a radiation source emits a pulse in proximity to a formation. In step 420, the resulting interactions between the pulse and the material of the formation result in time-dependent radiation from the formation that may be detected by the detectors 130, 120. Herein, the interactions may include, but are not limited to, inelastic scattering, neutron capture, pair production, Compton scattering, and the photoelectric effect. In step 430, the radiation information collected from the first detector 120 may be divided into at least two energy windows, wherein at least one of the energy windows is above the energy level required for pair production. In step 440, the radiation information collected from the second detector 130 may be divided into the at least two energy windows. In some embodiments, detector 120 may be the second detector and detector 130 may be the first detector. In some embodiments, three or more detectors may be used. While the gamma ray information from both detectors 120, 130 may be divided into the identical two energy windows, the first energy window of the first detector 120 may correspond to either the first energy window of the second detector or the second energy window of the second detector. Herein, energy windows may be referred to as "bins", "windows", and "peaks". The gamma ray information from the detectors may be used to generate time-dependent ratios between the radiation counts estimated by the detectors 120, 130. In the alternative, information collected by the detectors 120, 130 may be used to generate a difference between the radiation counts estimated by the detectors 120, 130. Since pair production may introduce errors into gamma ray information, these errors may be, optionally, reduced in step 450. In step 450, the gamma ray information from the first energy window of the first detector may be combined with the gamma ray information from the second energy window of the second detector to reduce an error in the gamma information due to pair production. In step 460, bulk density of the formation may be estimated using the corrected or uncorrected time-dependent ratios and applying them to the model. The estimation of the bulk density may also include comparison or combination of the time-dependent ratios with reference information about the formation. In some embodiments, estimation method 400 may include step 470, where reference information on the formation or formations is accessed. Reference information may be combined with time-dependent ratios in step 460 to estimate the bulk density. Within the model, the energy window used for the gamma ray information from the first detector and the energy window used for the gamma ray information from the second detector may be the same or different.

In embodiments where a pulsed radiation source is used, the attenuation of inelastic gamma rays and the propagation of captured gamma rays may be separated in time. This time separation may allow for radiation detector information to be separated not only in terms of the energy level of the gamma rays received but in terms of when the gamma rays are received by the detector, as it is well known that inelastic gamma rays do not arrive at the detectors at a time significantly after the end of the source pulse. Additionally, radiation information may be estimated for each individual detector or as an aggregate of radiation counts received by all detectors.

Figure 5:
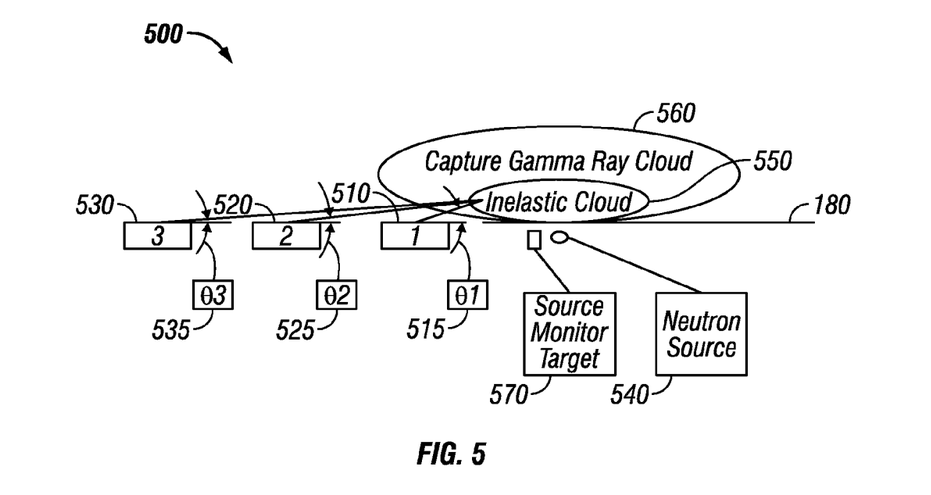
FIG. 5 shows a graphical illustration of the relationship between gamma ray detectors and gamma ray source clouds using one embodiment according to the present disclosure.

Since inelastic and capture gamma rays may be separated by their time of birth when using a controlled radiation source, such as a pulsed neutron source, pulsed gamma ray source, or pulsed X-ray source, they may also be separated (to a high degree) at the detectors in the time domain. This may result in the separation of inelastic gamma density estimates from capture gamma estimates and may also allow for pair production correction. Pair production removes a photon from the system, which if uncorrected, may result in an overestimated Compton Scattering probability. Compton scattering probability may be converted to bulk density by methods known to those skilled in the art. Capture gamma ray information may be more sensitive to neutron distribution changes than inelastic gamma ray information. This may be a result of the typical the capture gamma ray source cloud 560 being larger than the inelastic gamma cloud 550 and the small θ angle approximation may not be as valid for capture gamma rays as for inelastic gamma rays.

For sourceless density, transmission/attenuation estimates may be more reliable than Compton scattering estimates since the source magnitude and distribution does not need to be known. Bulk density may be estimated using a combination of inputs from multiple detectors. Compton scattering, capture gamma rays, and photoelectric cross section estimates may be used to forward model the bulk density and/or calculate a best estimate from multiple detectors.

In one embodiment, shown in FIG. 5, three scintillation detectors 510, 520, and 530 may be placed in line with a neutron source 540 within a downhole tool 500. The detectors 510, 520, and 530 may be placed at varying distances in a substantially linear pattern from the neutron source 540. A neutron target 570 may act as a source monitor. As will be understood by one of skill in the art, inelastic gamma rays may be generated in an inelastic gamma cloud 550 within the formation 180 relatively near the neutron source 540, and the capture gamma rays may be generated in a capture gamma cloud 560 within the formation 180 in a larger spatial distribution. Due to the location of the inelastic gamma clouds 550 and the capture gamma cloud 560 in the formation 180, the emitted gamma rays will reach the detectors 510, 520, 530 at respective angles $\theta$, 515, 525, 535.

When the angles $\theta$, 515, 525, 535 are small, a small angle approximation may be used in estimating how each detector will see the gamma clouds 550, 560 Angles $\theta$, 515, 525, 535 are smaller as the distance between the detectors 510, 520, 530 and neutron source 540 increases. If the results using a small angle approximation are undesirable, collimation may be used to improve the results. The effective source cloud 550, 560 location may be the average of the cloud as seen from the detectors' perspective, similar in concept to an adjoint response or detector sensitivity function. The effective cloud distance from the detectors 510, 520, 530 may be determined from the convolution of the detector adjoint function and the gamma ray distributions.

Under conditions where the small $\theta$ angle approximation holds true, each detector 510, 520, 530 may see the same effective source cloud location, and the path lengths between each detector and source clouds 550, 560 and the correlation of gamma ray physics to bulk density (electron density) may be known.

Under conditions where the small $\theta$ angle approximation may not hold true, difficulties caused by a relatively large inelastic or capture gamma cloud 560 may be mitigated by using collimation of the detectors 510, 520, 530. Collimation may force one or more detectors 510, 520, 530 to view the desired inelastic or capture gamma cloud 560 location and allow for correlation to electron and bulk density. Collimation may also be necessary due to high count rates at the near detector(s) to prevent saturation and pulse overlap which causes a loss of energy resolution.

Hydrogen and chlorine capture gamma rays originating from the borehole fluids may also reduce the accuracy of the bulk density estimate. A table of capture gamma ray energies is given later which shows that to avoid hydrogen and chlorine peaks, energy windows between approximately 2.4 and 5.8 MeV may be considered if a detector has 10% or better energy resolution. Other high-energy windows may not be used due to their high borehole dependence. A detector with poor energy resolution may overlap gamma ray peaks that originate from the borehole and formation at distinct energies, and this may reduce accuracy of bulk density estimation of the formation.

Since the gamma ray source strength may be unknown in a sourceless environment, count rate ratios may be used to eliminate dependence on knowledge of the gamma ray source strength. Bulk density may then be estimated using a model that relates the count rate ratios to bulk density of the formation. It will be understood by one of skill in the art that any gamma ray energy peak (window) may be used, not just the inelastic gamma rays used in this example.

Figure 6:
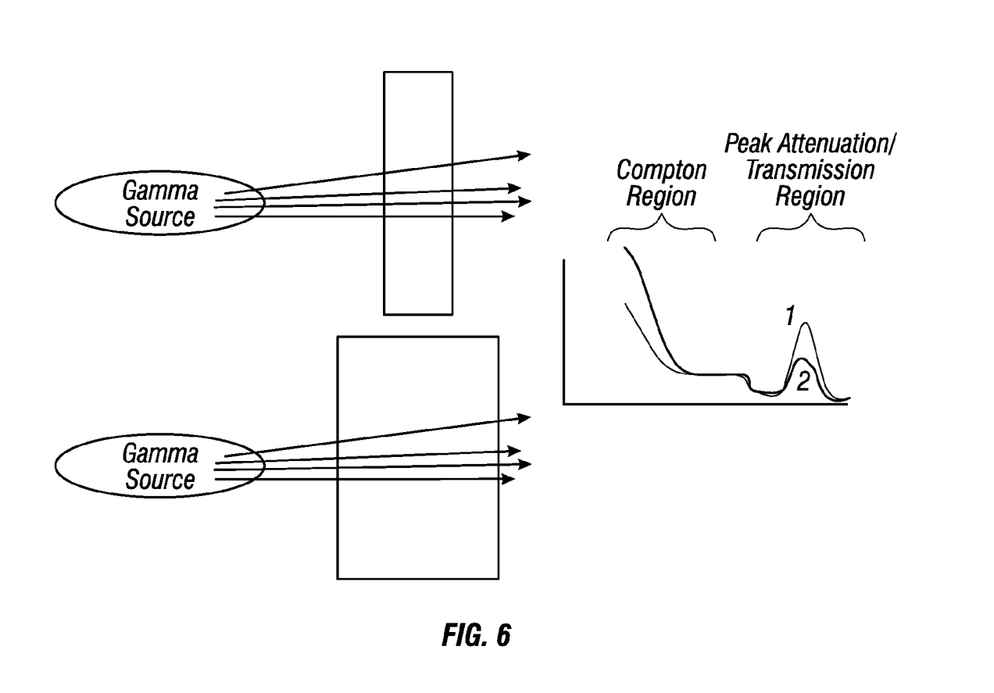
FIG. 6 shows a graphical illustration of attenuation of gamma rays through one-dimensional material layers for a monoenergetic source.

As shown in FIG. 6, the attenuation of a gamma ray source travelling through a one-dimensional slab of material may be measured by the reduction of radiation intensity in a measured spectrum. This attenuation may be correlated to electron and bulk density by taking ratios of the measured intensity, as further shown by (1) below. When $\theta$ is small, then the effective path length (t) from the inelastic gamma ray cloud to the detector may be invariant with respect to position variations of the source cloud. Also, gamma rays travel approximately the same path lengths through the formation and borehole for each detector. For each detector pair, the ratio of gamma ray count rates between two detectors may be expressed as follows:

$$\frac{I_a}{I_b} = e^{-\mu[t_a - t_b]}, \text{ where } a, b = 1, 2, 3 \quad (1)$$

where I is the counts within a single gamma ray peak or energy window, t is the path length, and $\mu$ is the linear attenuation coefficient. The difference of path lengths, $[t_a - t_b]$, is solely a function of the downhole tool layout when $\theta$ is small. Finally, the ratio of counts, $I_a/I_b$, is a function of $\mu$ which depends on A) electron density of the material for Compton scattering and B) pair production properties. A multidimensional equation for radiation attenuation may be used, as known by those skilled in the art.

Equation (1) relates the ratio of the peak (window) counts in each detector to the material's linear attenuation coefficient, which may be written as a function of electron density once pair production is accounted for. It is well known that electron density correlates to bulk density through the Z/A ratio, and the Z/A ratio is generally ~0.5.

The number of counts in a high-energy peak (window) will have contributions from gamma rays born within the peak (window) and experiencing only small-angle Compton scattering such that the gamma ray lost energy may be small in comparison to peak (window) size. The result is that the gamma rays remains in the energy window of their birth when detected. This effect may be lessened by the use of narrower peaks (windows). Obviously, if bulk high-energy gamma ray counts are obtained, this effect may be maximized.

In some conditions, it may be desirable to estimate bulk density of the formation using gamma rays at energy levels where a significant amount of the gamma rays are above the level required for pair production, such as in method 400. Estimates of bulk density may be improved when using method 400 by correcting for pair production. Pair production may physically correlate to the square of the atomic number of the material, $Z^2$, for total atomic pair production and then also as a function of energy of the gamma rays for each individual element. For lower Z materials, the pair production attenuation coefficient tends to be about one order of magnitude less than that of Compton scattering in the energies of interest (approximately 1-6 MeV). Hence, a correction may be necessary for accurate density estimates, but highly accurate corrective methods may not be required.

Pair production may be accounted for numerically from measured spectral information in multiple ways. Firstly, pair production may be numerically correlated to a measurement of the 511 keV peak due to positron annihilation. Accounting may need to be made for Compton scattering within the detector that also generates 511 keV photons. A priori knowledge of the detector material and a detector response function may be combined with the measured high-energy photon spectrum to calculate the 511 keV response due to pair production in the detector.

Figure 7:
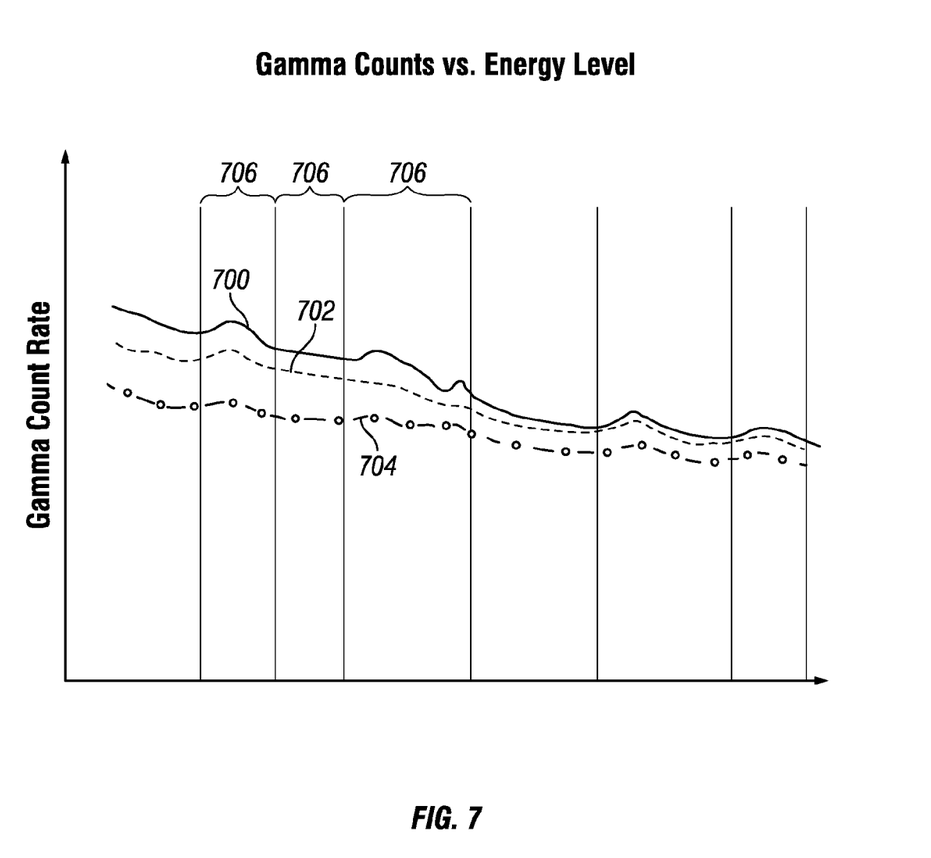
FIG. 7 shows a graphical illustration of gamma ray count rates divided into energy windows according to one embodiment of the present disclosure.
Figure 8:
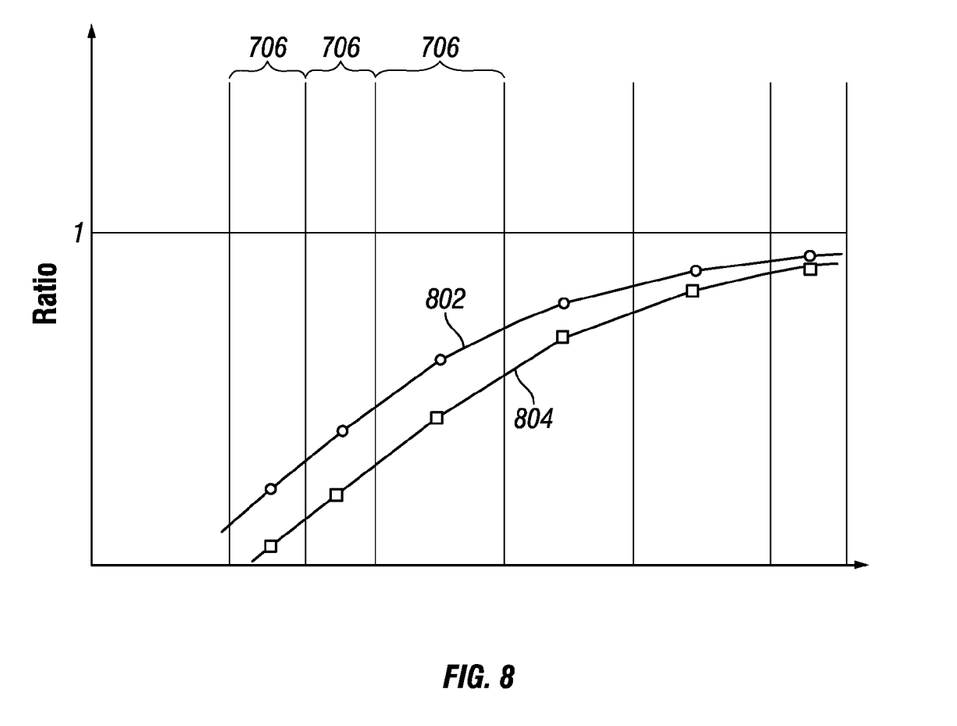
FIG. 8 shows a graphical illustration of gamma ray data ratios between detector pairs according to one embodiment of the present disclosure.

Pair production may also be accounted for by using multiple energy window ratios (or, peak reductions) to solve a system of linear equations in a direct or least squares sense to determine the pair production effect on the density measurement. Pair production may be parameterized for common formation materials as a function of energy and elemental composition. Further, if mineralogy of the formation is known, then these parameters tend to be known to a high degree. FIG. 7 illustrates sample gamma ray information obtained during step 430 from three detectors. The information may be expressed as curves 700, 702, 704 and divided into energy windows 706. These gamma ray information curve 700, 702, 704 may be expressed as ratios 802, 804 in step 440, as shown in FIG. 8 The ratios 802, 804 may be used, in step 450, to estimate bulk density. Higher energy windows 706 may tend to have higher pair production effects. Higher energy windows 706 may also be desirable due to a lower signal gain requirement and lower amounts of signal noise due to the lower signal gain requirement.

The series of linear equations (2) are as follows:

$$\frac{I_1}{I_2}\bigg|_{peak\ 1} = e^{-(\mu_{c,1}+\mu_{pp,1})[x_1-x_2]}$$

$$\vdots$$

$$\frac{I_1}{I_2}\bigg|_{peak\ p} = e^{-(\mu_{c,p}+\mu_{pp,p})[x_1-x_2]}$$

where I is the counts within a single gamma ray peak or energy window, x is the path length, $\mu_{c,p}$ is the linear attenuation coefficient due to Compton scattering for a given peak p, and $\mu_{pp,p}$ is the linear attenuation coefficient due to pair production for a given peak p. By separating the linear attenuation into Compton scattering and pair production components, optimizing the linear attenuation coefficient components may correct the bulk density estimate for pair production.

Finally, pair production may be accounted using a spine and rib based method where the ribs are used for quantifying pair production effects. A unique rib may be calculated for each energy peak and each material type. These ribs can be A) combined into a parameterized form to correct the bulk density estimates with no knowledge of lithology, B) used individually with a priori knowledge of approximate lithology, C) used individually with measured mineralogical composition, and D) collapsed to a single approximated rib (e.g. limestone density). The measure of peak reduction described above can be used to solve a system of equations in a least squares sense to determine the pair production correction (ribs).

In one embodiment, lower high-energy peaks may be used for an initial estimate of bulk density. Then, higher high-energy peaks may be used to estimate a pair production correction to the bulk density initial estimate. This strategy is employed because pair production effects increase with higher energy and Compton scattering decreases with higher energy. Thus, bulk density may be better estimated at lower energy peaks (windows) and pair production may be better estimated at higher energy peaks (windows).

If P peaks (windows) are acquired, and B windows used to solve for bulk density, then P-B windows may be used to solve a system of equations to correct for pair production. Thus, a (P-B) parameterization of the pair production cross section as a function of energy and material may be made. Correction for borehole effects may lessen this order of parameterization accordingly. Alternatively, if the low-energy Compton regions of the spectra are correlated to environmental effects, the pair production order of parameterization may not be lessened.

As shown in FIG. 2, method 200 relies on using inelastic gamma rays rather than capture gamma rays. Capture gamma rays may initiate from a wider source distribution, however, they are typically subject to environmental effects. Inelastic gamma rays result from high energy neutrons that are mostly unaffected by variations in the environment. Inelastic gamma rays may be formed in a smaller spatial distribution, which may increase the validity of the assumption of θ being small. Method 200 may be implemented with each pair of detectors, and may result in $N*P_{inelastic}$ ratios for inelastic gamma rays and $N*P_{capture}$ ratios for capture gamma rays, where P is the number of peaks or windows in capture and inelastic mode and N is the number of gamma ray detectors. Any number of energy windows may be used, and the width of the energy windows depends primarily on the energy window count rate achievable by the logging specifications.

Using ratios of detector count rates amongst N detectors for P number of peaks may be plotted, resulting in improved estimates of bulk density. The ratios may be used to eliminate the need for knowledge of the radiation source magnitude.

With $N*P+3$ degrees of freedom, where P is the number of unique energy peaks of windows used in calculations, P may be further divided as $P=P_{inelastic}+P_{capture}$. These extra degrees of freedom may be used to form an environmentally corrected weighted average of the bulk density that is more accurate than any single measurement alone. Each measurement contains approximations to the physics present in the environment that can be minimized through a least squares, or similar, combination of multiple measurements.

Additionally, count rate magnitudes and differences may be used when the neutron source output is known. The accuracy of the resulting first order scaling may be improved with knowledge of the lithology of the formation.

As shown in FIG. 4, method 400 relates to adding pair production correction to the well known method of relating bulk density to Compton scattered gamma rays. Comparing Compton regions at each of the three detectors may provide up to three more estimates of bulk density, or degrees of freedom to use for corrections. This is due to the Compton scattering energy relationship that shows that any gamma ray that significantly scatters 1-2 times from high energies will generally be lowered to within the region of 200-1000 keV. This allows for relative (ratio-based) comparison of Compton counts without knowledge of the source strength. Due to the presence of chlorine and hydrogen, Compton region counts should be acquired only during the inelastic time periods to avoid the larger source distribution of capture gamma rays with borehole effects. Similarly, bulk density may also be estimated using a photoelectric cross section of the formation.

Figure 9:
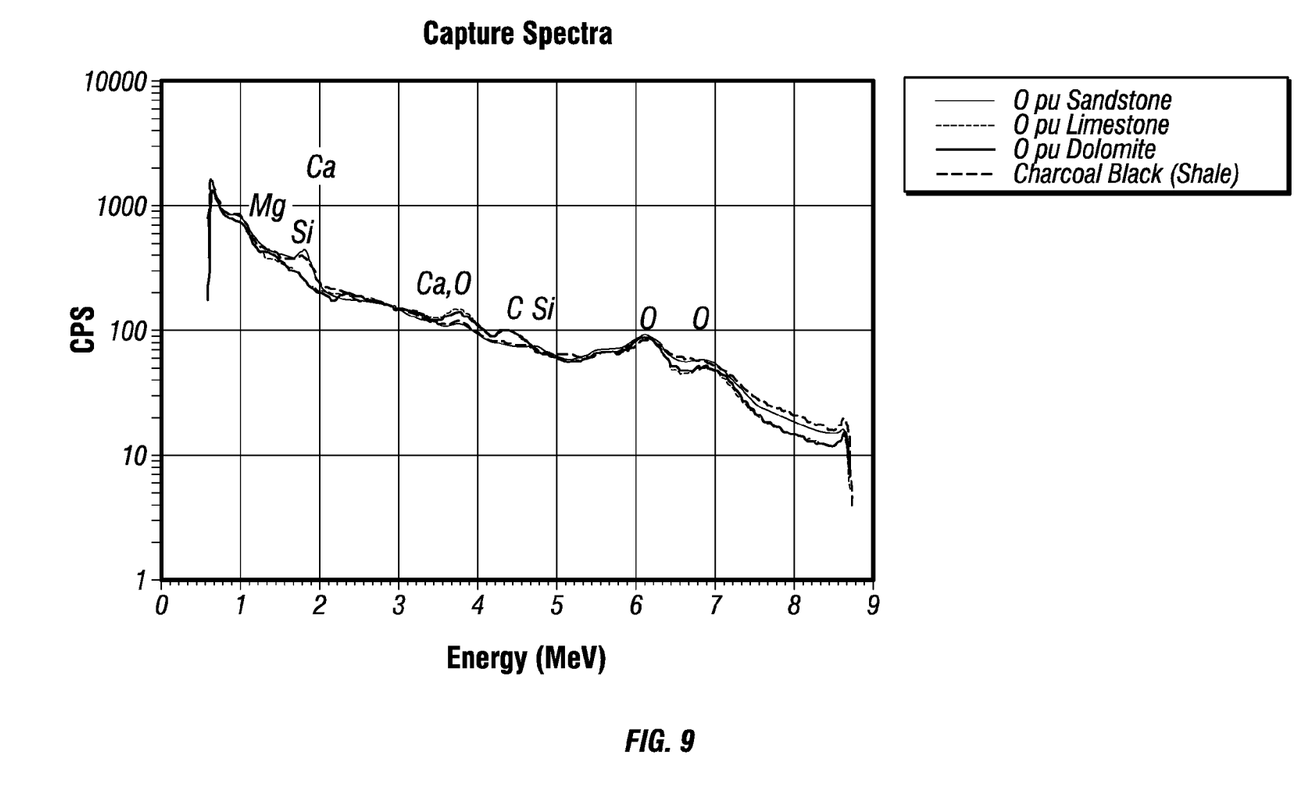
FIG. 9 shows a graphical illustration of inelastic gamma rays detected in known formation materials using one embodiment according to the present disclosure.
Figure 10:
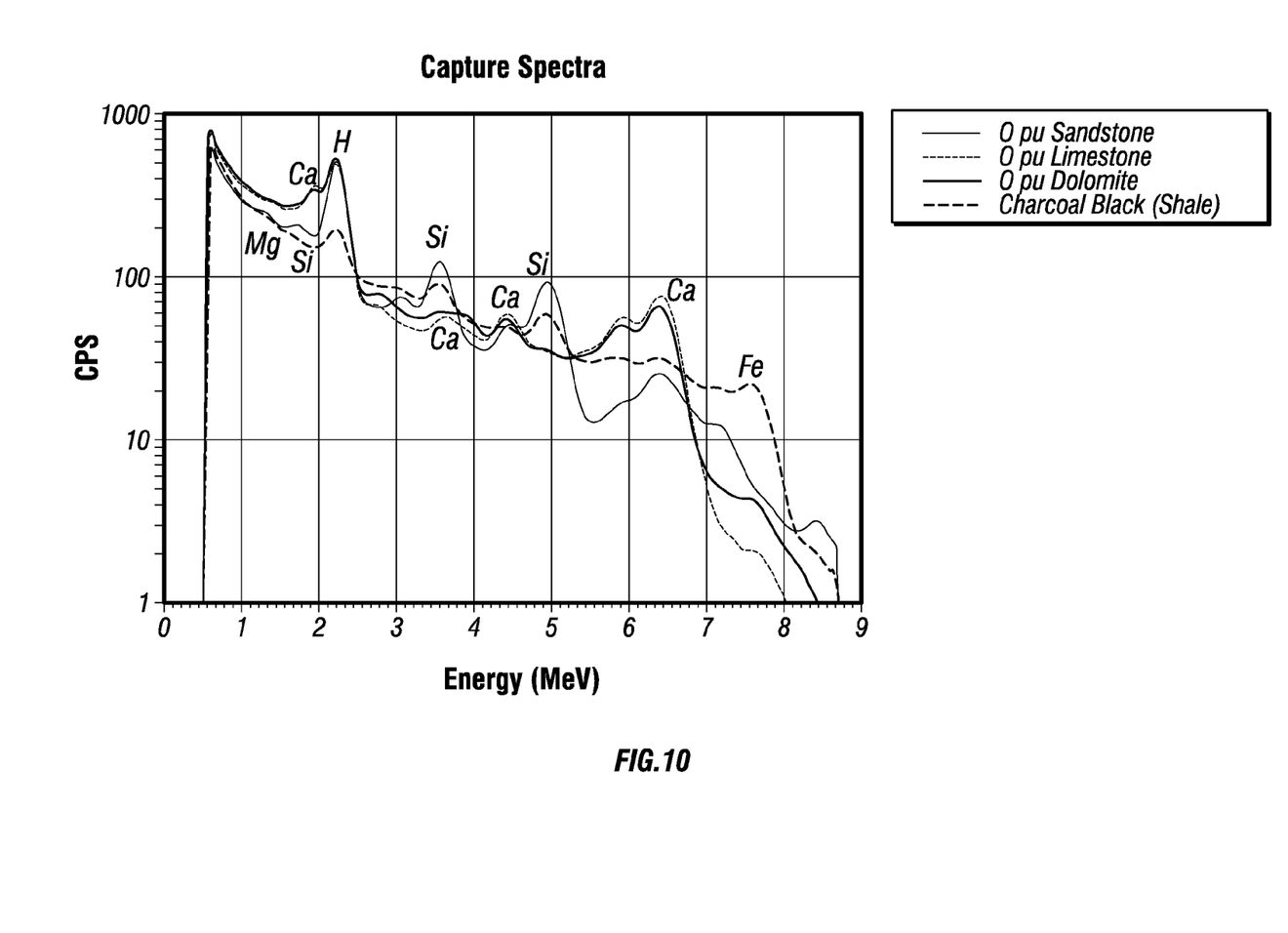
FIG. 10 shows a graphical illustration of capture gamma rays detected in known formation materials using one embodiment according to the present disclosure.

An example of inelastic and capture energy peaks measurable by a detector in typical formations is shown in FIGS. 9 & 10 for Limestone, Sandstone, and Dolomite. Potential gamma ray sources are listed in the following table which may each be used for inelastic and capture energy peaks. A peak finder routine or energy window generator may determine the presence of peaks in real time in acquired spectra for variable unknown lithologies. Alternatively, the complete spectra above 1 MeV may be subdivided into capture and inelastic energy windows beforehand based on expected count rates. This will waste zero counts in the detectors above 1 MeV for inelastic. For capture, the hydrogen and chlorine regions can be avoided to minimize borehole fluid effects.

| Element | Inelastic Gamma Ray (MeV) | Capture Gamma Ray (MeV) |
| --- | --- | --- |
| Si | 1.779 | 3.5, 4.9 |
| O | 3.7, 6.1, 7.0 | |
| Ca | 3.76 | 1.9, 4.4, 6.2 |
| H | | 2.2 |
| Cl | | 0.787, 1.165, 1.954, 6.112 |

In some embodiments, either high/low energy resolution and high/low density scintillation detectors may be used based on the use of energy peak or energy window methodologies employed. To identify peaks effectively, energy resolution may be made a priority. The use of energy windows does not require peak identification and may allow for the use of lower energy resolution detectors. As is common with scintillators, lower energy resolution detectors may be optimized or selected for higher densities, higher temperature, and higher count rate performance, as desired for a particular embodiment.

A density image may be acquired from this disclosure with azimuthal information recording. Vertical resolution may be a function of detector spacing and methodology employed in calculating a best estimate using information from each detector. Azimuthal resolution may depend on detector shielding and division of count rates into sectors. In Wireline measurements where significant invasion occurs, correction for resolution may be made with the multiple energy peak (window) approach.

Correction for neutron activation of the environment and subsequent radioactive decay may be made through the measurement of background when the neutron source has been off for sufficiently long time that capture gamma rays have been extinguished.

Shielding of the detectors may be implemented for neutrons and gamma rays. Gamma ray shielding prevents the detection of gamma rays from behind the tool and from that originating within the tool. Neutron shielding prevents neutrons from reaching the detector regions and inducing gamma rays. Combinations of neutron moderators, neutron absorbers, high hydrogen content epoxies, and high-density high-Z materials are known to those skilled in the art.

While the foregoing disclosure is directed to the one mode embodiments of the disclosure, various modifications will be apparent to those skilled in the art. It is intended that all variations be embraced by the foregoing disclosure.

I claim:

1. A method for estimating a bulk density of an earth formation, comprising:
estimating the bulk density with a processor using a model relating inelastic gamma ray information above an energy level required for pair production acquired from a first detector to inelastic gamma ray information acquired from a second detector;
wherein the estimating includes:
dividing the inelastic gamma ray information acquired from the first detector into at least two energy windows, wherein a first energy window of the at least two energy windows is above the energy level required for pair production;
dividing the inelastic gamma ray information acquired from the second detector into the at least two energy windows; and
reducing an error due to pair production using the inelastic gamma ray information acquired from the first detector in the first energy window and the inelastic gamma ray information acquired from the second detector in a second energy window of the at least two energy windows.

2. The method of claim 1, further comprising:
exposing the earth formation to at least one of: (i) an X-ray source, (ii) a gamma ray source, and (iii) a neutron source.

3. The method of claim 1, wherein the inelastic gamma ray information acquired from the first and second detectors includes at least one of: a gamma count and a gamma rate.

4. The method of claim 1, wherein the model uses a mathematical relationship between the inelastic gamma ray information above the energy level required for pair production acquired by the first detector and the inelastic gamma ray information acquired by the second detector, wherein the inelastic gamma ray information acquired by the second detector is above an energy level required for pair production, and wherein the mathematical relationship is one of: (i) a ratio and (ii) a difference.

5. The method of claim 1, wherein bulk density is estimated by solving for $\mu$ in the equation:

$$\frac{I_a}{I_b} = e^{-\mu[t_a - t_b]},$$

where:
$I_a$: gamma ray value from the first detector,
$I_b$: gamma ray value from the second detector,
$t_a$: distance between the first detector and an emission source,
$t_b$: distance between the second detector and the emission source.

6. The method of claim 1, further comprising:
obtaining the inelastic gamma ray information using the first and second detectors.

7. The method of claim 1, wherein the inelastic gamma ray information from the first and second detectors is time-dependent.

8. The method of claim 1, further comprising:
obtaining capture gamma ray information from the first detector and the second detector.

9. The method of claim 1, wherein the second energy window is the first energy window.

10. An apparatus for estimating bulk density of an earth formation, comprising:
at least one processor;
a non-transitory computer-readable medium; and
a program stored by the non-transitory computer readable medium comprising instructions that, when executed, cause the at least one processor to:
estimate the bulk density using a model relating inelastic gamma ray information above an energy level required for pair production acquired from a first detector to inelastic gamma ray information acquired from a second detector;
wherein the instruction include further instructions that, when executed, cause the at least one processor to:
divide the inelastic gamma ray information acquired from the first detector into at least two energy windows, wherein a first energy window of the at least two energy windows is above the energy level required for pair production;
divide the inelastic gamma ray information acquired from the second detector into the at least two energy windows; and reduce an error due to pair production using the inelastic gamma ray information acquired from the first detector in the first energy window and the inelastic gamma ray information acquired from the second detector in a second energy window of the at least two energy windows.

11. The apparatus of claim 10, wherein the program further comprises instructions that, when executed, cause the at least one processor to:

expose the earth formation to at least one of: (i) an X-ray source, (ii) a gamma ray source, and (iii) a neutron source.

12. The apparatus of claim 10, wherein the inelastic gamma ray information from the first detector and the second detector includes at least one of: a gamma count and a gamma rate.

13. The apparatus of claim 10, wherein the model uses a mathematical relationship between the inelastic gamma ray information above the energy level required for pair production acquired by the first detector and the inelastic gamma ray information acquired by the second detector, wherein the inelastic gamma ray information acquired by the second detector is above an energy level required for pair production, and wherein the mathematical relationship is one of: (i) a ratio and (ii) a difference.

14. The apparatus of claim 10, wherein bulk density is estimated by solving for $\mu$ in the equation:

$$\frac{I_a}{I_b} = e^{-\mu[t_a - t_b]},$$

where:
$I_a$: gamma ray value from the first gamma detector,
$I_b$: gamma ray value from the second gamma detector,
$t_a$: distance between the first gamma detector and an emission source,
$t_b$: distance between the second gamma detector and the emission source.

15. The apparatus of claim 10, wherein the program further comprises instructions that, when executed, cause the at least one processor to:

obtain the inelastic gamma ray information using the first and second detectors.

16. The apparatus of claim 10, wherein the inelastic gamma ray information from the first and second detectors is time-dependent.

17. The apparatus of claim 10, wherein the program further comprises instructions that, when executed, cause the at least one processor to:

obtain capture gamma ray information from the first and second detectors.

18. The apparatus of claim 10, wherein the second energy window is the first energy window.

* * * * *